United States Patent [19]

Watts et al.

[11] Patent Number: 4,737,487

[45] Date of Patent: Apr. 12, 1988

[54] VIP TYPE PEPTIDES

[75] Inventors: Eric A. Watts, Harlow; Gordon Wootton, Sawbridgeworth; Christine Summers, Sturmer, all of England

[73] Assignee: Beecham Group p.l.c., Brentford, England

[21] Appl. No.: 793,245

[22] Filed: Oct. 31, 1985

[30] Foreign Application Priority Data

Nov. 1, 1984 [GB] United Kingdom ............... 8427651

[51] Int. Cl.$^4$ .................... A61K 37/02; C07K 7/06
[52] U.S. Cl. ..................................... 514/15; 514/16; 530/327; 530/328
[58] Field of Search ................... 514/12, 15, 16; 530/324, 326, 327, 328

[56] References Cited

U.S. PATENT DOCUMENTS

| | | | |
|---|---|---|---|
| 3,862,927 | 1/1975 | Said et al. | 530/326 |
| 3,898,329 | 8/1975 | Said et al. | 514/12 |
| 4,016,258 | 4/1977 | Said et al. | 530/324 |
| 4,237,046 | 12/1980 | Bodanszky . | |
| 4,605,641 | 8/1986 | Bolin et al. | 514/12 |

OTHER PUBLICATIONS

A. Couvineau et al., "Structural Requirements for VIP Interaction with Specific Receptors in Human and Rat Intestinal Membranes: Effect of Nine Partial Sequences", *Biochemical and Biophysical Research Communications*, 121, pp. 493–498 (1984).

M. Bodanszky et al., "A Preferred Conformation in the Vasoactive Intestinal Peptide (VIP), Molecular Architecture of Gastrointestinal Hormones", *Bioorganic Chemistry*, 3, pp. 133–140 (1974).

H. C. Beyerman et al., "Synthesis, Biological & Immunological Properties of Analogs of Secretin and Vasoactive Intestinal Peptide (VIP); the Vasectrins", *Chem.*
Oct. 11, 1984 [WO] PCT Int'l Appl. ... PCT/JP84/00476
Feb. 15, 1985 [WO] PCT Int'l Appl. ... PCT/JP85/00062

M. Bodanszky et al., "Vasoactive Intestinal Peptide (VIP). VI. 17—Norleucine Analog of the Sequence 14–28", *Chem. Abs.*, vol. 82, p. 57 (1975): Bioorg. Chem., 3(3), pp. 320–323 (1974).

G. Wendlberger et al., "Total Synthesis of the 17—Norleucine Analog of Porcine Vasoactive Intestinal Polypeptide (VIP), *Chem. Abs.*, vol. 98, p. 544 (1983): Pept. Proc. Eur. Pept. Symp., 16th, pp. 209–295 (Pub. 1981).

*Primary Examiner*—Delbert R. Phillips
*Attorney, Agent, or Firm*—James F. Haley, Jr.; Teresa L. Solomon

[57] ABSTRACT

Peptides comprising, in sequence, units selected from the amino acid residues 11 to 23 of vasoactive intestinal peptide (VIP) and consisting at least of the amino acid residues 15 to 20, or an analogue thereof wherein one or more of the amino acid residues is replaced by an equivalent other amino acid, or a pharmaceutically acceptable salt thereof; having pharmacological activity, a process for their preparation and their use as pharmaceuticals.

9 Claims, No Drawings

VIP TYPE PEPTIDES

Vasoactive intestinal peptide comprises a peptide having a sequence of 28 amino acids in a single chain. The sequence of VIP (pig) is shown in table 1.

TABLE 1: VIP (pig)

N—Terminus

His - Ser - Asp - Ala - Val - Phe - Thr - Asp - Asn - Tyr - Thr - Arg - Leu - Arg - Lys - Gln - Met - Ala - Val - Lys - Lys - Tyr - Leu - Asn - Ser - Ile - Leu - Asn—NH$_2$

C—Terminus

The invention relates to VIP fragments and analogues, processes for their preparation, pharmaceutical preparations containing them and their use in medicine.

Vasoactive intestinal peptide (VIP) was originally isolated from the small intestines of the hog, but it has since been isolated from other species, such as the chicken, and has been shown to have a wide distribution throughout body tissues.

It has systemic vasodilator activity. It includes systemic hypotension and increases cardiac output on intravenous infusion. It increases hepatic arterial blood flow, increases blood sugar levels, and has the ability to bring about tracheal relaxation, and relaxation of gut smooth muscle, as well as stimulation of the output of bicarbonate from intestinal secretions. It therefore appears to be useful in treatment of hypertension and peripheral vascular disease on parenteral administration, and as a bronchodilator on aerosol or parenteral administration.

Abbreviations used are as follows:

| Amino Acid Residue | Abbreviations |
| --- | --- |
| alanine | Ala |
| arginine | Arg |
| asparagine | Asn |
| aspartic acid | Asp |
| glutamine | Gln |
| histidine | His |
| isoleucine | Ile |
| leucine | Leu |
| lysine | Lys |
| methionine | Met |
| norleucine | Nle |
| phenylalanine | Phe |
| serine | Ser |
| threonine | Thr |
| tyrosine | Tyr |
| valine | Val |

The amino acid components are in the L-form.

VIP (chicken) is closely related, differing in the 11, 13, 26 and 28 positions; the peptide has:

a serine residue in position 11,
a phenylalanine residue in position 13,
a valine residue in position 26 and
a threonine residue in position 28.

A number of C-terminal fragments have been produced, mostly in the synthetic programme required to prove the structure of VIP. Few structures have been obtained from the N-terminus, and very little work has been carried out on fragments from the centre of the molecule.

It has, however, been concluded (Robberecht, Gut Hormones (1978) edited by Bloom, p 97 to 103) that the C-terminus of VIP holds the receptor recognition site, and that the N-terminus holds the activation site, together with a minimal capacity for binding.

Counter to the commonly held views regarding the activity of VIP, we have found that there is pharmacological activity even in the absence of the amino acid units at the C- and N-termini of the molecule.

The present invention provides a peptide comprising, in sequence, units selected from the amino acid residues 11 to 23 of VIP and consisting at least of the amino acid residues 15 to 20, or an analogue thereof wherein one or more of the amino acid residues is replaced by an equivalent other amino acid.

The present invention also provides a peptide consisting, in sequence, of the VIP units selected from the amino acid residues 11 to 23, and comprising at least the amino acid residues 15 to 20, or an analogue thereof having pharmacological activity.

Preferably in a peptide of the present invention the amino acid units are selected from residues 13 to 23 or 11 to 21, more especially from residues 13 to 21, of VIP. In an analogue thereof, one or more than one amino acid unit may be replaced by an equivalent amino acid unit.

Amino acids can be considered as members of different classes; such groupings are well known. Replacement of an amino acid of the peptide by an equivalent amino acid may be by another amino acid of the same class, and where an amino acid can be grouped into two or more classes, replacement may be made from one or more of these classes.

All amino acids in an analogue of the present invention may, for example, be naturally occurring amino acids, i.e. L-amino acids, or amino acids in the D- or DL-form.

It seems reasonable to suppose that the activity of a peptide bears some relationship to its secondary structure (which could be inherent, or adopted at the receptor site). Thus the expressed activity could be related to a potential for formation of a highly ordered arrangement of some of the amino acids.

Where there is replacement of one or more amino acids, the replacement may, for example, be such that the essential structure of the fragment is maintained.

Without intending to be limited to the following hypothesis, we presently believe it is possible that, for peptides of the present invention, a helical structure may be a contributory factor in the pharmacological activity. The replacing amino acid or acids in an analogue thereof may therefore, if desired, be selected so as to have at least as good a helical-forming character as the replaced amino acid(s). However, lack of a helical structure may not impair the activity of a peptide or analogue of the present invention; for example, it may be preferred, for pharmacological reasons or otherwise, to incorporate D-amino acid(s) as the replacing amino acid(s) and it will, of course, be understood that unless all amino acids in the resulting analogue are in the D-form, the structure will not be of a helical nature.

Thus, for example:

the threonine at position 11 of VIP (pig) may, if desired, be replaced by another hydroxy amino acid, e.g. serine (Ser); and the serine at position 11 of VIP (chicken) may, if desired, be replaced by another hydroxy amino acid, e.g. threonine (Thr);

the arginine at position 12 and/or at position 14 may, if desired, be replaced by another basic amino acid, e.g. lysine (Lys) or ornithine (Orn);

the leucine at position 13 of VIP (pig) and/or at position 23, and the phenylalanine at position 13 of VIP (chicken) may, if desired, be replaced by another hydrophobic amino acid, in the case of leucine, by, for example, valine (Val), and, in the case of phenylalanine, by, for example, tyrosine;

the lysine at any one or more of positions 15, 20 and 21 may, if desired, be replaced by another basic amino acid, e.g. ornithine (Orn) or arginine (Arg);

the glutamine at position 16 may, if desired, be replaced by another carboxamido amino acid, e.g. asparagine (Asn);

the methionine at position 17 may, if desired, be replaced by another neutral amino acid, e.g. the isosteric norleucine (Nle) or leucine (Leu);

the alanine at position 18 may, if desired, be replaced by another hydrophobic amino acid, e.g. glycine (Gly) or norvaline (Nva);

the valine at position 19 may, if desired, be replaced by another hydrophobic amino acid, e.g. leucine (Leu);

the tyrosine at position 22 may, if desired, be replaced by another hydrophobic amino acid, especially an aromatic amino acid, e.g. phenylalanine (Phe).

Especially, there should be mentioned analogues in which one or more of the amino acid residues 15 to 20 is replaced by an equivalent other amino acid and any additional amino acid residues present correspond to those in VIP.

Especially, the present invention provides a hexapeptide amide with the amino acid sequences of the residue 15 to 20 of VIP, or an analogue thereof in which one or more of the amino acids is replaced as indicated above.

Very especially, the present invention provides the hexapeptide

Lys Gln Y Ala Val Lys where Y represents Met or Nle; and also the hexapeptide

Lys Gln Y Ala Leu Lys where Y represents Met or Nle.

Fragments and analogues of VIP (pig) should especially be mentioned, but the basic structure may correspond to VIP from any source.

The following fragments and analogues should especially be mentioned:

```
                    Arg [A];
                Leu Arg [A];
            Arg Leu Arg [A];
        Thr Arg Leu Arg [A];
                        [A] Lys;
                        [A] Lys Tyr;
                        [A] Lys Tyr Leu;
                    Arg [A] Lys;
                    Arg [A] Lys Tyr;
                    Arg [A] Lys Tyr Leu;
                Leu Arg [A] Lys;
                Leu Arg [A] Lys Tyr;
                Leu Arg [A] Lys Tyr Leu;
            Arg Leu Arg [A] Lys;
            Arg Leu Arg [A] Lys Tyr;
            Arg Leu Arg [A] Lys Tyr Leu;
        Thr Arg Leu Arg [A] Lys;
        Thr Arg Leu Arg [A] Lys Tyr;
        Thr Arg Leu Arg [A] Lys Tyr Leu.
``` where
[A] denotes Lys Gln Y Ala Val Lys
in which Y represents Met or Nle.

The amino acids may, for example, be in the L-form; although one or more D-amino acids may, if desired, be present in the structure.

The carboxy-terminus of the peptides or analogues of the present invention may be in the form of the acid (—OH); an ester, for example an alkyl ester, especially a ($C_1$-$C_4$)-alkyl ester, e.g. the methyl ester, (—OCH$_3$), the hydrazide (—NH—NH$_2$), or an amide, usually the unsubstituted amide (—NH$_2$). Preferably the carboxy-terminus is in the form of the unsubstituted amide.

The amino-terminus of the peptides or analogues of the present invention may be in the form of the unsubstituted amine (—NH$_2$) or protected amine (—NHR) where R represents, for example, acetyl or tert.-butyloxycarbonyl, or benzyloxycarbonyl, or in the form of an acid addition salt, preferably a physiologically tolerable, pharmaceutically acceptable acid addition salt, of the amine.

Acid addition salts may be, for example, salts with inorganic acids such, for example, as hydrochloric acid, hydrobromic acid, orthophosphoric acid or sulphuric acid, or organic acids such, for example, as methanesulphonic acid, toluenesulphonic acid, acetic acid, trifluoroacetic acid, propionic acid, lactic acid, citric acid, tartaric acid, fumaric acid, malic acid, succinic acid, salicylic acid or acetylsalicylic acid.

Thus, more particularly, the present invention provides a polypeptide of the general formula $$X—(Y')_n—Y_{15}Y_{16}Y_{17}Y_{18}Y_{19}Y_{20}—(Y'')_m—Z \quad I$$

in which
X represents a hydrogen atom or an amine-protecting group, preferably a hydrogen atom;
$(Y')_n$ represents a direct bond or

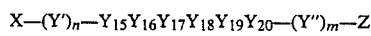

in which
$Y_{11}$ represents Thr, Ser or the residue of another hydroxy amino acid,
$Y_{12}$ represents Arg or the residue of another basic amino acid,
$Y_{13}$ represents Leu, Phe or the residue of another hydrophobic amino acid,
$Y_{14}$ represents Arg or the residue of another basic amino acid;
$Y_{15}$ represents Lys or the residue of another basic amino acid, e.g. Orn,
$Y_{16}$ represents Gln or the residue of another carboxamido amino acid,
$Y_{17}$ represents Met or the residue of another neutral amino acid, e.g. Nle,
$Y_{18}$ represents Ala or the residue of another hydrophobic amino acid,
$Y_{19}$ represents Val or the residue of another hydrophobic amino acid,
$Y_{20}$ represents Lys or the residue of another basic amino acid, e.g. Orn,
$(Y'')_m$ represents a direct bond or $$Y_{21}, Y_{21}Y_{22} \text{ or } Y_{21}Y_{22}Y_{23}$$

in which
$Y_{21}$ represents Lys or the residue of another basic amino acid,
$Y_{22}$ represents Tyr or the residue of another hydrophobic amino acid,
$Y_{23}$ represents Leu or the residue of another hydrophic amino acid; and
Z represents a hydroxyl group, or a group of the formula OR such that COZ represents an ester, or a hydrazino group such that COZ represents a hydrazide, or NH$_2$ such that COZ represents an amide, preferably NH$_2$; and salts thereof, preferably physiologically tolerable salts thereof, especially physiologically tolerable acid addition salts thereof.

The compounds of formula I are preferably in pharmaceutically acceptable form. By pharmaceutically acceptable form is meant, inter alia, of a pharmaceutically accpetable level of purity excluding normal pharmaceutical additives such as diluents carriers, and including no material considered toxic at normal dosage levels. A pharmaceutically acceptable level of purity will generally be at least 50% excluding normal pharmaceutical additives, preferably 75%, more preferably 90% and still more preferably 95%.

A peptide or analogue of the invention may be prepared by those methods known in the art for the synthesis of compounds of analogous structure and in this regard reference is made, by way of illustration only, to the following literature:
(a) Y. S. Klausner and M. Bodanszky, *Bioorg. Chem.* (1973), 2, p 354–362.
(b) M. Bodanszky, C. Yang Lin and S. I. Said, *Bioorg. Chem.* (1974), 3, p 320–323.
(c) S. R. Pettit, "*Synthetic Peptides*", (Elsevier Scientific Publishing Co. 1976).
(d) Stewart and Young, "*Solid Phase Peptide Synthesis*" (W. H. Freeman and Co. 1969).

(e) E. Atherton, C. J. Logan and R. C. Sheppard, *J. C. S. Perkin I*, (1981) p 583–546.

(f) E. Brown, R. C. Sheppard and B. J. Williams, *J. C. S. Perkin I*, (1983) p 1161–1167.

The present invention also provides a peptide or analogue of the present invention which has been prepared synthetically.

A peptide or analogue of the present invention may, for example, be formed by the sequential coupling of appropriate amino acids or by the initial preparation and subsequent coupling of peptide subunits, themselves prepared in stepwise manner; in either case either classical solution chemistry methods of peptide synthesis or solid phase procedures may be used.

The coupling reactions may be effected by, for example, activating the reacting carboxyl group of the ingoing amino acid, and reacting this with the amino group of the substrate unit. Details of suitable, optional activating and protecting (masking) groups and of suitable reaction conditions (for the coupling reactions and for the introduction and removal of protecting groups) giving, preferably, the minimum of racemisation, may be found in the above-referenced literature.

Accordingly, the present invention further provides a process for the preparation of a peptide or analogue of the present invention, which comprises coupling a suitable amino acid or amino acid sequence in which the carboxyl group is activated with an appropriate amino acid or amino acid sequence and repeating, if necessary, the coupling procedure until there is obtained a peptide comprising, in sequence, units selected from the amino acid residues 11 to 23 of VIP consisting at least of the amino acid residues 15 to 20, or an analogue thereof in which one or more of the amino acid residues is replaced by an equivalent other amino acid, wherein, if desired or required, non-reacting functional groups are protected during the coupling procedure and, if desired, subsequently deprotected.

A polypeptide of the general formula I may thus be prepared by reacting a reagent of the general formula $$H-Y^1-OH \qquad (II)$$

wherein $Y^1$ represents an amino acid unit or a partial radical sequence identical with the corresponding N-terminal amino acid unit or partial radical sequence in formula I, with a reagent of the general formula $$H-Y^2-OH \qquad (III)$$

wherein $Y^2$ represents an amino acid unit or a partial radical sequence identical with that in the balance of the above-defined product peptide, the reagents (II) and (III) being optionally protected and/or activated where and as appropriate, followed if desired or required by one or more of the following:
deprotection of the products,
conversion of one carboxy terminus into another carboxy terminus,
conversion of a free peptide into a salt thereof.

For example, an appropriate peptide ester of the general formula $$X-Y^1-Y^2-OR \qquad (IV)$$

wherein X, $Y^1$ and $Y^2$ have the meanings given above and R represents, for example, an alkyl group and preferably an alkyl group having 1 to 4 carbon atoms, may be converted into an amide by reaction with ammonia.

Compounds of the general formulae II, III and IV may themselves be prepared by standard techniques analogous to those described above.

It will be appreciated that a protected forms of a peptide or analogue of the present invention are useful novel intermediates and form an aspect of the invention.

A peptide or analogue of the present invention may also be prepared on a solid phase support, for example a polyamide or a polystyrene resin, using amino acids protected at the N-terminus, for example with the fluorenylmethyloxycarbonyl group or the t-butyloxycarbonyl group and with appropriate protection of any side-chain functional groups.

One such reaction scheme for solid-phase peptide synthesis is, for example, illustrated below.

Solid Phase Scheme

A.A. = Amino acid
t-BOC = t-Butyloxycarbonyl
Fmoc = Fluorenylmethyloxycarbonyl, i.e.

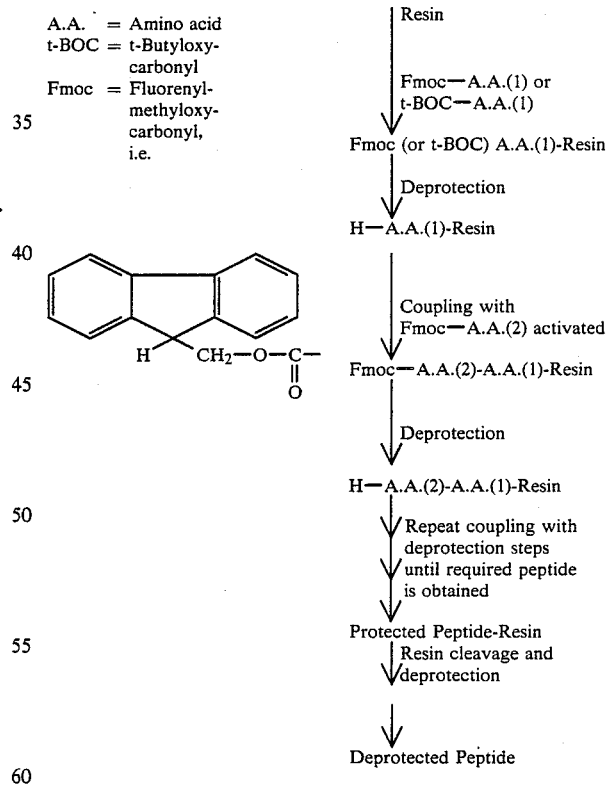

This technique involves the addition of the first protected amino acid to a solid resin support. After removal of the protecting group (deprotection) the amino acid-resin is coupled with the next protected amino acid in its activated form. The deprotection/coupling procedures are repeated until the required peptide is obtained. The peptide is then cleaved from the resin before final removal of the protecting groups Alternatively, when desired or necessary, the protecting groups may be removed before cleavage of the peptide from the resin.

Advantageously the Fmoc group is the form of protection used for the α-amino function of the amino acids involved (but not for side chain protection).

However, the last amino acid in each synthesis is generally protected as its t-BOC or FMOC derivative. This allows the peptide to remain fully protected on cleavage from the resin.

The use of alternative resins may also require the need for removal of protecting groups prior to resin cleavage. In this case it is likely that the Fmoc-protecting group would be used for N-alpha protection throughout the syntheses.

The peptides and analogues of the present invention have smooth muscle relaxant activity such as gastro-intestinal, bronchodilator and vasodilator actions, and in addition, anti-ulcer activity. They may be useful in preventing the pain and constipation frequently encountered in some irritable bowel syndrome (IBS) patients and may be a useful new approach to duodenal ulcer therapy.

The present invention further provides a peptide or analogue of the present invention, for use in a method of treatment of the human or animal body.

Where the fragment or analogue is in the form of a salt thereof, it should of course be understood that this is a physiologically tolerable salt, which is pharmaceutically acceptable.

The peptide or analogue of the invention may be administered per se or, preferably, as a pharmaceutical composition also including a pharmaceutically suitable carrier.

Accordingly, the present invention provides a pharmaceutical composition, which comprises a peptide or analogue of the present invention, in admixture or conjunction with a pharmaceutically acceptable carrier.

The preparation may, if desired, be in the form of a pack accompanied by written or printed instructions for use.

In accordance with conventional pharmaceutical practice the carrier may comprise a diluent, filler, disintegrant, wetting agent, lubricant, colourant, flavourant or other conventional additive.

Preferably, a pharmaceutical composition of the invention is in unit dosage form.

The suitable dosage range for compounds of the invention may vary from compound to compound and may depend on the condition to be treated. It will also depend, inter alia, on the relation of potency to absorbability and on the mode of administration chosen.

Suitable formulations are, for example, intravenous infusions, aerosols and enteric coated capsules.

The present invention further provides a method of treatment of a human or non-human animal, which comprises administering an effective, non-toxic, amount of a peptide or analogue of the present invention to a human or non-human animal; and a peptide or analogue of the present invention for use as a pharmaceutical, in particular for the treatment of disorders and complaints described below.

A peptide or analogue of the present invention may be used to treat the following disorders and complaints; abnormalities of gut motility, e.g. hypermotility as in IBS or oesophageal spasm; peptic ulceration; bronchial spasm; vascular conditions such as hypertension and ischaemia; mental disorders.

Conveniently, the active ingredient may be administered as a pharmaceutical composition hereinbefore defined, and this forms a particular aspect of the present invention.

A suitable dose is, for example, in the range of from 1 μg to 2.5 mg/kg i.v. in the rat. A possible daily dose for humans is, for example, 0.01 to 50 mg by intravenous infusion, 0.01 to 250 mg by aerosol or 0.1 to 500 mg by enteric coated capsule.

No adverse toxicological effects are indicated at the aforementioned dosage ranges.

In the following, the various derivatives protecting groups, reagents and solvents are referred to by abreviations for convenience.

| Derivatives, Protecting Groups, Reagents, Solvents | Abbreviated Designation |
| --- | --- |
| Tertiary-butyl | $Bu^t$ |
| Tertiary-butyloxycarbonyl | t-Boc |
| N—hydroxysuccinimide ester | OSu |
| Methyl ester | OMe |
| Trifluoroacetic acid | TFA |
| Dicyclohexylcarbodiimide | DCC |
| Benxyloxycarbonyl | CBZ |
| Dimethylformamide | DMF |
| Tetrahydrofuran | THF |
| p-Nitrophenyl ester | ONP |
| Hydrochloride salt | .HCl |
| Ethyl acetate | EtOAc |
| Methanol | MeOH |
| Ammonium Acetate | $NH_4OAc$ |
| 1-Hydroxybenzotriazole | HOBT |
| Chloroform | $CHCl_3$ |
| Pyridine | Pyr |
| n-Butanol | BuOH |
| Ammonium hydroxide | $NH_4OH$ |
| Sodium hydrogen carbonate | $NaHCO_3$ |
| Sodium chloride | NaCl |
| Ether | $Et_2O$ |
| Sodium sulphate | $Na_2SO_4$ |
| Potassium hydroxide | KOH |
| Acetic acid | AcOH |

T.L.C. (Merck) silica gel plates) with solvent systems
$E_4$ MeOH—$CHCl_3$ (1:9)
H n-BuOH:AcOH:Pyr:$H_2O$ (15:3:10:12)
$A_3$ n-BuOH:AcOH:$H_2O$ (4:1:1)

EXAMPLE 1

H-Lys-Gln-Nle-Ala-Val-Lys-$NH_2$ (V)

The hexapeptide amide (V) was prepared as illustrated in Scheme I and the experimental details are given below.

Scheme 1

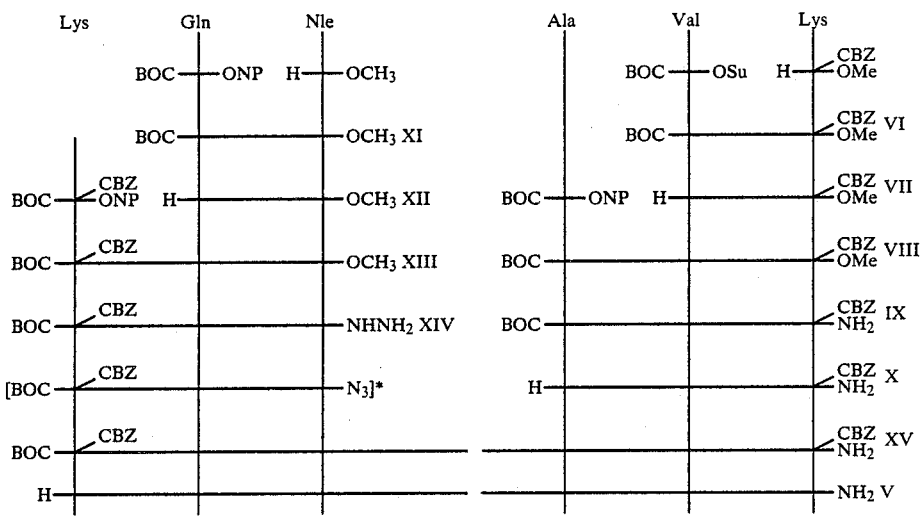

*Prepared in situ.

t-Boc-Val-Lys(CBZ)-OMe (VI)

A mixture of t-Boc-Val-OSu (3.14 g, 10 mmol) and H-Lys(CBZ)-OCH$_3$.HCl (3.31 g, 10 mmol) in THF (300 ml) was treated at room temperature with triethylamine (1.38 ml) and left stirring for 17 hr. The resulting solution was evaporated in vacuo and the residue was dissolved in EtOAc (500 ml). The organic solution was washed successively with water (2×200 ml), 5% citric acid (2×200 ml), water (2×200 ml) and dried over Na$_2$SO$_4$. The dried solution was filtered and evaporated in vacuo to give (VI) (4.9 g; 99%) as a foam. T.l.c. R$_f$E$_4$=0.64.

H-Val-Lys(CBZ)-OMe trifluoroacetate (VII)

The protected dipeptide (VI) (4.9 g, 10 mmol) was dissolved in TFA (20 ml) and stirred for 10 minutes at room temperature. The solution was evaporated in vacuo, azeotroped with toluene (2×20 ml) and triturated with Et$_2$O (2×50 ml). The mother liquors were decanted to leave the partially deprotected dipeptide as the trifluoroacetate salt VII (2.41 g; 51% R$_f$E$_4$=0.22.

t-Boc-Ala-Val-Lys(CBZ)-OMe (VIII)

(VII) 2.4 g, 6.1 mmol) was added to t-Boc-Ala-ONP (1.9 g, 6.1 mmol) in THF (50 ml) containing triethylamine (0.85 ml). The mixture was stirred at room temperature for 4 days, evaporated in vacuo and partitioned between EtOAc (250 ml) and water (100 ml). The organic layer was washed successively with 0.45M NH$_4$OH (4×50 ml), 2% citric acid (4×50 ml) and water (4×50 ml). The organic layer was dried over Na$_2$SO$_4$, filtered and evaporated in vacuo. The residue was recrystallised from EtOAc-hexane to give (VIII) (1.62 g; 47%) as colourless microcrystals, mp 104° C. [α]$_D^{26}$=−48° C. (C=1, MeOH).

t-Boc-Ala-Val-Lys(CBZ)-NH$_2$ (IX)

(VII) (2.0 g, 35 mmol) was added to a solution of ammonia (ca. 50 ml) in methanol (50 ml). The mixture was kept in a sealed pressure vessel for 24 hrs, then evaporated to dryness. The residue was taken up in EtOAc, evaporated to dryness and triturated with Et$_2$O give (IX) (1.75 g; 90%) as colourless microcrystals mp 195°-196° C. [α]$_D^{26}$=−48.8° (C=1, MeOH).

H-Ala-Val-Lys(CBZ)-NH$_2$.trifluoroacetate (X)

The protected tripeptide amide (IX) (1.0 g, 1.8 mmol) was dissolved in cold TFA (10 ml). After 10 minutes, the mixture was evaporated in vacuo and the residue was triturated with ether (2×50 ml). The mother liquors were decanted and the residue was dried under vacuum to give (X) as a foam (0.85 g; 83%).

t-Boc-Gln-Nle-OMe (XI)

t-Boc-Gln-ONP (12.3 g, 32 mmol) and HOBT (5.0 g, 37 mmol) were added to a solution of H-Nle-OMe.HCl (5.99 g, 33 mmol) and triethylamine (4.9 ml) in DMF (55 ml).

The mixture was stirred at room temperature overnight, EtOAc (100 ml) was added and the organic phase was washed with 2% citric acid, 0.45M NH$_4$OH until free of nitrophenol, 5% NaHCO$_3$, 2% citric acid, water until neutral, and a saturated solution of NaCl. The solution was dried over Na$_2$SO$_4$, filtered and concentrated in vacuo. Petroleum ether (bpt 40°-60° C.) was added, the precipitate was filtered, washed with the same solvent and dried in vacuo over silica gel to give (XI) (10.2 g, 85%) mpt 108°-109° C., [α$_D^{26}$=−14.89° (C−1, DMF), T.l.c. R$_f$A$_3$=0.72.

H-Gln-Nle-OMe.trifluoroacetate (XII)

The protected dipeptide ester (XI) (4.8 g, 13 mmol) was dissolved in cold TFA (40 ml). After 10 minutes, the TFA was removed in vacuo and dry ether (200 ml) was added. The ether was decanted and the residue was washed with more ether (100 ml). The oily material was dried over KOH to give (XII) as a white foam that was used immediately, T.l.c. R$_f$A$_3$=0.42.

BOC-Lys(CBZ)-Gln-Nle-OMe (XIII)

H-Gln-Nle-OMe.TFA salt (XII) (13 mmol) triethylamine (1.76 ml, 13 mmol), HOBT (2.16 g, 16 mmol) and BOC-Lys(CBZ)-ONP (7.6 g, 15 mmol) were dissolved in DMF (30 ml). The reaction mixture was kept basic with small amounts of triethylamine. The mixture was stirred overnight at room temperature, concentrated in vacuo and treated with unsymmetrical dimethylethylenediamine (2 equivs). After 2 hours, EtOAc was added and the product was isolated as described for compound (XI). The solid was washed with petroleum ether (bpt 40°-60° C.) and dried in vacuo over silica gel to give (XIII) (5.5 g; 65%) $[\alpha_D{}^{26} = -16.49°$ (C=1, DMF) T.l.c. $R_fA_3$ 0.8.

BOC-Lys(CBZ)-Gln-Nle-NHNH$_2$ (XIV)

The tripeptide methyl ester (XIII) (1 g, 1.6 mmol) was suspended in DMF (5 ml), hydrazine (0.8 g, 0.78 ml, 16 mmol) was added and the mixture was stirred overnight. The solvent was removed in vacuo and the residue solidified using MeOH/EtOAc to give (XIV) (0.9 g, 90%). T.l.c. $R_fA_3 = 0.70$ This was used immediately in the next step.

t-Boc-Lys(CBZ)-Gln-Nle-Ala-Val-Lys(CBZ)-NH$_2$ (XV)

(XIV) 0.58 g, 0.9 mmol) was dissolved in anhydrous DMF (18 ml) and cooled to $-30°$ C. 4.56M HCl in dioxane (0.90 ml) was added followed by t-butyl nitrite (0.12 ml). The reaction was left for 30 to 40 min at $-30°$ C. then cooled to $-60°$ C. Triethylamine (0.60 ml) was added followed by the deprotected amide (X) (0.384 g, 0.68 mmol) and a further addition of triethylamine (0.1 ml). The mixture (M) was left to stand, reaching ambient temperature over 2 days. A further amount of (XIV) (0.29 g, 0.45 mmol) in DMF (10 ml) was treated at $-30°$ C. with 4.5M HCl in dioxane (0.45 ml), t-butyl nitrite (0.06 ml) and triethylamine (0.3 ml) as described above and added to the reaction mixture (M) at $-30°$ C. The whole was left to stand, reaching ambient temperature over a further 4 days.

The mixture was evaporated in vacuo and the residue was triturated with EtOAc:MeOH (1:1) (50 ml) to give (XV) (0.62 g; 85%) as a greyish solid.

H-Lys-Gln-Nle-Ala-Val-Lys-NH$_2$ (V)

The protected hexapeptide (XV) (0.2 g, 0.2 mmol) was dissolved in TFA (5 ml) and treated with HBr gas over 1 hr. The mixture was evaporated in vacuo and triturated with Et$_2$O (2×50 ml) to give (V) as a *hydrobromide salt* (0.13 g) $R_fH = 0.14$. This and a subsequent batch of product were purified by adsorption on to an ion exchange column (CM 25 Sephadex, Pharmacia) which was washed with 10-100 mmol NH$_4$OAc at pH 7. The product was eluted with 100 mmol NH$_4$OAc at pH 8.5. Lyophilisation and subsequent preparative HPLC [μBondapak ODS.; CH$_3$CN: 50 mmol NH$_4$OAc(aq) (15:85) gave (V) as an *acetate salt* (0.15 g) mp 253°-255° C. T.l.c. $R_fH = 0.14$, MH$^+$ (FAB) = 685.

EXAMPLE 2

H-Arg-Lys-Gln-Nle-Ale-Val-Lys-Lys-NH$_2$.Acetate (XVI)

The octapeptide amide (XVI) was prepared as illustrated in Scheme II and in the experimental details given below.

t-Boc-Lys(CBZ)-Lys(CBZ)-OCH$_3$ (XVII)

A mixture of t-Boc-Lys-(CBZ)-OH (1.14 g, 3 mmol), Lys-(CBZ)-OCH$_3$.HCl (0.99 g, 3 mmol), DCC (0.62 g, 3 mmol), HOBT (0.41 g, 3 mmol) and triethylamine (0.42 ml) in dry amine-free DMF (20 ml) was stirred for 17 h. Work up as described for VI gave XVII (1.2 g; 61%) as colourless microcrystals, mp 109°-110° (ex acetone-light petroleum 40°-60°) $[\alpha]_D{}^{26} = -11.9°$ (C=1 MeOH) $R_fE_4 = 0.71$.

H-Lys-(CBZ)-Lys-(CBZ)-OCH$_3$.trifluoroacetate (XVIII)

The protected dipeptide (XVII) (1.8 g, 2.7 mmol) was partially deprotected as for VII to give XVIII as a foam (1.8 g; 99%) $R_fE_4 = 0.22$.

t-Boc-Val-Lys-(CBZ)-Lys-(CBZ)-OCH$_3$ (XIX)

A mixture of t-Boc-Val-OSu (0.86 g 2.7 mmol), XVIII (1.8 g, 2.7 mmol) and triethylamine (0.4 ml) in THF (50 ml) was stirred, under N$_2$, for 2 days. Work up as described for VI gave XIX (1.25 g; 60%) as colourless microcrystals, mp 145°-147° (ex EtoAc) $R_fE_4 = 0.40$ $[\alpha]_D{}^{26} = -24.59°$ (C=1 MeOH).

H-Val-Lys-(CBZ)-Lys-(CBZ)-OCH$_3$.trifluoroacetate (XX)

The protected tripeptide XIX (2.16 g, 2.9 mmol) was partially deprotected as for VII to give XX as a flaky solid (2.02 g; 92%).

Boc-Ala-Val-Lys-(CBZ)-Lys-(CBZ)-OCH$_3$ (XXI)

A mixture of XX (2.0 g), Boc-Ala-ONP (1.0 g, 3.2 mmol), HOBT (0.80 g) and triethylamine (0.50 ml) was stirred at room temperature in DMF (5 ml) for 24 h. The mixture was evaporated to ¼ volume and taken up into CHCl$_3$ (100 ml). The organic solution was washed successively with 0.45M NH$_4$OH (4×50 ml), 2% citric acid (4×50 ml) and water (4×50 ml). The organic layer was dried over Na$_2$SO$_4$, filtered and evaporated in vacuo to ¼ volume. The solution was chromatographed on Kieselgel 60 PF$_{254}$ on a 'Chromatotron' and the product was eluted with an increasing concentration of MeOH (0–5%) in CHCl$_3$ to give XXI (1.98 g; 84%) as colourless microcrystals, mp 175°-177° $[\alpha]_D{}^{26} = -36.89$ (C=1 MeOH). MH$^+ = 827$ (FAB).

Boc-Ala-Val-Lys-(CBZ)-Lys-(CBZ)-NH$_2$ (XXII)

XXI (1.78 g, 2.2 mmol) was added to a solution of ammonia (ca. 50 ml) in methanol (50 ml). The mixture was kept in a sealed vessel for 48 h. The resulting precipitate was filtered, washed with dry Et$_2$O to give XXII (1.78 g; 98%) as colourless microcrystals mp 243°-244°.

H-Ala-Val-Lys-(CBZ)-Lys-(CBZ)-NH$_2$.trifluoroacetate (XXIII)

The protected tetrapeptide XXII (1.75 g, 2.2 mmol) was suspended in acetic acid (3 ml), cooled to 10° and treated with TFA (9 ml). The solution was stirred for 20–25 min. Work-up as described for VII gave XXIII (1.71 g) R$_f$E$_1$=0.7.

H-Lys-(CBZ)-Gln-Nle-OMe (XXIV)

The protected tripeptide ester (XIII) (2.0 g, 3 mmol) was dissolved in cold TFA (12.6 ml) and glacial acetic acid (5.4 ml). After 25 minutes, the solvents were removed in vacuo and dry ether (100 ml) was added. The ether was decanted and the residue was washed with more ether (100 ml). The oily material was dried in vacuo over KOH to give the *trifluoroacetate salt* of (XXIV) as a white foam. The foam was dissolved in water (40 ml) and a cold solution of sodium carbonate (0.15 g) in water (10 ml) added. The free base was extracted into ethyl acetate (100 ml, then 4×30 ml) and this organic phase was washed with water (2×20 ml), saturated NaCl (20 ml), dried over Na$_2$SO$_4$, filtered and evaporated in vacuo to give XXIV (1.5 g; 89%). T.l.c. R$_f$=0.3 in 30% MeOH/CHCl$_3$.

BOC-Arg(H+)-Lys-(CBZ)-Gln-Nle-OMe (XXV)

The free amine (XXIV) (1.5 g, 2.8 mmol) was dissolved in DMF (9 ml). The solution was cooled, then BOC-Arg(H+)OH (1.23 g, 4.5 mmol), DCC (0.82 g, 4 mmol) and HOBT (0.57 g, 4 mmol) were added. After 2 hours, additional portions of BOC-Arg(H+)OH (0.45 g, 1.6 mmol), DCC (0.3 g, 1.5 mmol) and HOBT (0.2 g, 1.6 mmol) were added and the reaction was allowed to proceed for 3 days.

The dicyclohexylurea was removed by filtration and washed with DMF (3×5 ml). The solvent was removed in vacuo and the residue was applied in methanol to a Sephadex LH-20 column (2.5×100 cm) pre-equilibrated with the same solvent. Fractions of 5 ml were collected at a flow rate of 1 ml/3 mins. The fractions containing the desired product were pooled, evaporated and re-chromatographed under the same conditions.

The product was further purified on Kieselgel 60 Pf$_{254}$ using a 'Chromatotron' (20% MeOH/CHCl$_3$ as eluant) to give (XXV) (1.3 g, 56%) $[\alpha]_D^{26}$=−24.9° (C=1, MeOH).

BOC-Arg(H+)-Lys-(CBZ)-Gln-Nle-NHNH$_2$ (XXVI)

The tetrapeptide methyl ester (XXV) (1.3 g, 1.6 mmol) was suspended in methanol (6 ml), hydrazine hydrate (0.8 g, 0.78 ml, 1.6 mmol) was added, and the stirring was continued for 6 hours. The product was filtered, washed with cold methanol (3×10 ml), water (8×5 ml), and dried in vacuo to give (XXVI) (1.2 g; 92%). The product was used immediately.

BOC-Arg(H+)-Lys-(CBZ)-Gln-Nle-Ala-Val-Lys-(CBZ)-Lys-(CBZ)-NH$_2$.Chloride (XXVII)

The protected tetrapeptide (XXVI) (0.37 g, 0.45 mmol) was dissolved in anhydrous DMF (5 ml) and cooled to −30°. 4.56M HCl in dioxane (0.45 ml) was added followed by t-butylnitrite (0.06 ml). The reaction was left for 30–40 min at −30° then cooled to −60°. Triethylamine (0.30 ml) was added followed by the deprotected amide XXIII (0.28 g, 0.3 mmol) and a further addition of triethylamine (0.05 ml). The mixture M$_2$ was left to stand, reaching ambiant temperature over 2 days. A further amount of XXVI (0.21 g, 0.26 mmol) in DMF (5 ml) was treated at −30° C. with 4.56M HCl in dioxane (0.25 ml), t-butyl nitrite (0.04 ml) and triethylamine (0.17 ml) as described above and added to the reaction mixture M$_2$ at −30° C. The whole was left to stand, reaching ambiant temperature over a further 4 days.

The mixture was treated with methanol and the whole centrifuged. The resulting solid and mother liquors were both shown to contain the desired product XXVII (1.25 g) MH+=1471 (FAB).

H-Arg-Lys-Gln-Nle-Ala-Val-Lys-Lys-NH$_2$.Acetate (XVI)

The protected octapeptide (XXVII) (1.25 g, 0.85 mmol) was dissolved in TFA at 10° and treated with hydrogen bromide gas for 2 h. The whole mixture was evaporated in vacuo, triturated with ether (4×15 ml) and filtered to give the free peptide as its hydrobromide salt (1.0 g). The peptide was purified with concomitant conversion to an *acetate salt, XVI* (0.22 g) (MH+ (FAB)=969) in the same manner as that described for (V).

SCHEME II

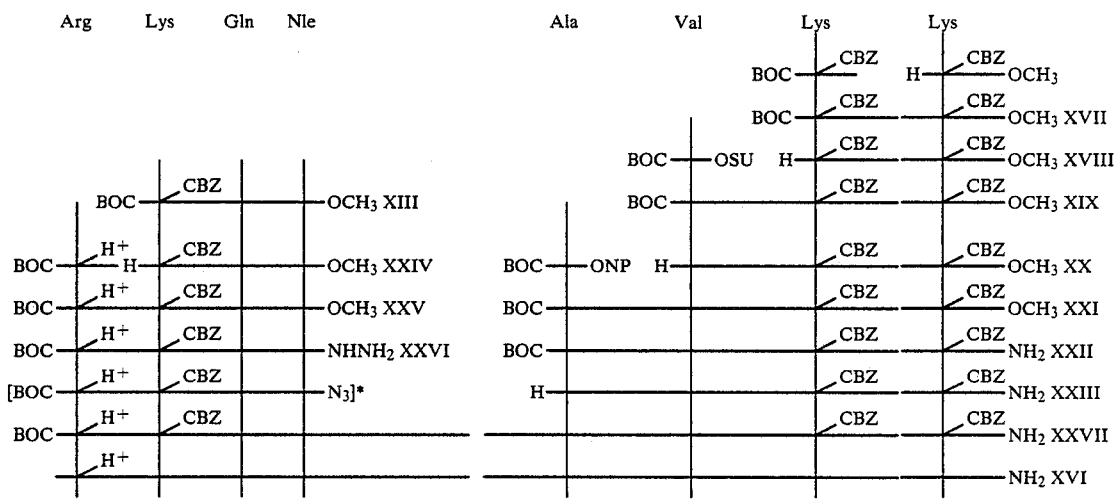

*Prepared in situ

Solid Phase Synthesised Peptides (a) The following examples were synthesised by solid phase methods using the 4-hydroxymethylbenzoylnorleucyl derivatised polydimethylacrylamide gel resin Pepsyn B (1.0 mequiv/g or 0.3 mequiv/g) as supplied by Cambridge Research Biochemicals Ltd.

DMF was fractionally distilled in vacuo from ninhydrin before use and stored over pre-activated molecular sieves (4 A). Piperidine was freshly distilled from a suitable drying agent. Dichloromethane (A.R.) was dried over pre-activated molecular sieves (4 A).

The amino acids were chosen as their Fmoc-derivatives with BOC- to t-Bu- side chain protection where necessary.

The symmetrical anhydride of the first amino acid (2.5 equiv), (prepared as described by E. Brown et al in J.C.S. Perkin I, 1983, 80) was added to the resin (1 equiv) in DMF (10-15 ml) in the presence of a catalytic quantity of dimethylaminopyridine. The mixture was agitated with $N_2$ and the reaction was allowed to proceed for 1 h. The resin was drained and the addition procedure was repeated. The drained resin was then washed with DMF (10-15 ml×1 min×10). The removal of the Fmoc protecting groups was achieved by agitation of the peptide-resin with piperidine (10 ml; 20% DMF) for 3 min then 7 min.

Subsequent addition of each amino acid was carried out using the Fmoc symmetrical amino acid anhydrides (2.5 equiv) or the preformed hydroxybenzotriazole ester (3.0 equiv) (from Fmoc-amino acid, DCC and HOBT).

Amino acids containing amidic side chains (e.g. Gln or Asn) were coupled as their p-nitrophenyl activated esters (3.0 equiv) in the presence of hydroxybenzotriazole (6.0 equiv).

Fmoc-Arginine was coupled to the peptide resin via its hydroxybenzotriazole ester. This was prepared by suspending Fmoc-Arginine (10 equiv) in DMF (10 ml) and adding HOBT (30 equiv). The clear solution was added to the resin and agitated for 1 minute. DCC (10 equiv) was then added and the reaction was allowed to proceed to completion.

The final amino acid in the chosen sequence was added as its Nα Boc derivative either as the symmetrical anhydride or as the preformed hydroxybenzotriazole ester.

Boc-Arginine was coupled as its hydrochloride and activated by addition of DCC (5 equiv) to the protected hydrochloride salt (10 equiv) in DMF (10-15 ml) 5 minutes prior to addition of the whole reaction mixture to the peptide-resin (1 equiv).

In some cases, Fmoc-amino acid anhydrides (eg Phe, Ala, Gly) coprecipated with DCU during their formation. In these cases, the anhydrides were prepared in the presence of 10% DMF in dichloromethane. Dichloromethane was removed in vacuo before addition of the whole mixture to the peptide resin. Couplings in general were carried out for 1-2 h and repeated if necessary. Completeness of acylation was verified by a qualitative Kaiser ninhydrin test as described by E. Kaiser et al in Anal. Biochem. (1970) p. 34.

Peptide cleavage from the resin was accomplished via ammonolysis to provide the protected peptide amide. To this end, when the final coupling was complete, the peptide-resin was washed with DMF (10-15 ml×1 min×10), anhydrous dichloromethane (10-15 ml×1 min×10) and dry ether (10 ml×1 min×10). The collapsed resin was dried over silica gel for 1 hour in a vacuum desiccator: The resin was re-swollen as previously described, drained and treated with a saturated solution of ammonia in methanol at −10°. The vessel was sealed and allowed to reach ambiant temperatures for 2 days. The apparatus was cooled, opened and the contents were allowed to warm to room temperature. The suspension was filtered under suction and the resulting residue was washed with methanol (5×5 ml) and DMF (5×5 ml). The combined washings and filtrate were evaporated in vacuo. The resulting residue was triturated with dry ether and filtered to give the protected peptide.

The final acidolytic deprotection procedure removed all protecting groups (e.g. BOC, t-Bu) from the peptide amide. Thus the protected peptide was dissolved in trifluoroacetic acid (4 ml/100 mg of peptide) and stirred at room temperature for 3 h. In some cases, hydrogen bromide gas was bubbled though the mixture during this time. The mixture was evaporated in vacuo and the resulting solid was triturated with dry ether (7×5 ml) to give the required peptide either as its trifluoroacetate or its hydrobromide salt. The peptides were purified by one or a combination of methods listed below.

(a) Conversion to acetate salt

The peptide salt was dissolved in a minimum amount of water and passed down a strong anion exchange resin which was in its acetate form (e.g. Sephadex QAE-A-25). Eluant was fractionated and the fractions containing desired materials were lyophilised.

(b) Selective adsorbtion chromatography

The peptide salt was dissolved in a minimum amount of water and adsorbed onto a weak cation exchange resin (e.g. Sephadex CM-25). The peptide acetate was recovered during elution with an increasing concentration of $NH_4OAc$ (0.05M–0.5M) at pH 7, an increasing pH gradient (pH 7–pH 9) or a combination of both.

(c) High Performance Liquid Chromatography.HPLC

The peptide was purified by preparative HPLC on reverse phase $C_{18}$ silica columns (e.g. μbondapak, Hypersil ODS).

The peptides were characterised by 24 h acidolytic cleavage and PITC derivatised amino acid analysis (Waters Picotag system) and fast atom bombardment (FAB) mass spectrometry (Jeol DX 303).

EXAMPLE 3

H-Leu-Arg-Lys-Gln-Nle-Ala-Val-Lys-Lys-NH$_2$.Acetate (XXVIII)

XXVIII was prepared using the 0.3 mequiv/g Pepsyn B resin.

[MH]+ =1081 (FAB).

Amino acid analysis. Glu (1.0) Arg (1.0) Ala (1.0) Val (0.88) Nle (1.0) Leu (1.0) Lys (2.88).

EXAMPLE 4

H-Lys-Gln-Nle-Ala-Leu-Lys-NH$_2$.Acetate (XXIX)

XXIX was prepared using the 1.0 mequiv/g Pepsyn B resin. [MH]+ (FAB)=699. Amino acid analysis; Glu (0.9), Ala (0.8), Leu (0.8), Nle (0.8), Lys (1.8).

EXAMPLE 5

H-Lys-Gln-Nle-Ale-Val-Orn-NH$_2$.Acetate (XXX)

XXX was prepared using the 1.0 mequiv/g Pepsyn B resin [MH]+ (FAB)=671. Amino acid analysis; Glu (1.01), Ala (0.9), Val (0.8), Nle (1.1), Lys (1.0), Orn (1.1).

EXAMPLE 6

H-Orn-Gln-Nle-Ala-Val-Orn-NH$_2$.Acetate (XXXI)

XXXI was prepared using the 1.0 mequiv/g Pepsyn B resin [MH]+ (FAB)=657.

EXAMPLE 7

H-Lys-Gln-Leu-Ala-Val-Lys-NH$_2$.Acetate (XXXII)

XXXII was prepared using the 1.0 mequiv/g Pepsyn B resin [MH]+ (FAB)=685.

EXAMPLE 8

H-Arg-Lys-Gln-Nle-Ala-Val-Lys-Lys-Tyr-Leu-NH$_2$.Acetate (XXXIII)

XXXIII was prepared using the 0.3 mequiv/g Pepsyn B resin. [MH]+ (FAB)=1245.

EXAMPLE 9

H-Lys-Gln-Nle-Ala-Val-Lys-Lys-Tyr-Leu-NH$_2$.Acetate (XXXIV)

XXXIV was prepared using the 0.3 mequiv/g Pepsyn B resin. [MH]+ (FAB)=1089.

(b) Use of the Beckmann model 990B Peptide Synthesiser

The following example was synthesised using leucine resin ester. This was prepared by reacting chloromethylated resin (3.5 g, 0.7 mequiv Clg$^{-1}$; 1% cross-linked styrene/divinylbenzene as supplied by Merseyside Laboratories) at 50° C., for 17 h, in DMF (40 ml) with the anhydrous cesium salt obtained from Boc-L-leucine monohydrate (0.5 g, 2 mmol). The resulting Boc-L-leucine resin ester was exhaustively washed with DMF, 50% aqueous DMF, $H_2O$, DMF and finally $CH_2Cl_2$, then dried (3.68 g; 0.22 mmol leucine/g).

Removal of the BOC group (from 3.6 g resin) was achieved by reaction with 50% TFA in $CH_2Cl_2$ (50 ml) for 5 min then 25 min. The leucine resin ester salt was washed with $CH_2Cl_2$ (7×50 ml), neutralised with 10% di-isopropylamine in $CH_2Cl_2$ for 5 min (3×50 ml) and washed with $CH_2Cl_2$ (8×50 ml).

The first amino acid of the required sequence was coupled to the leucine resin ester by the following procedure. Fmoc-L-tyrosine-t-butyl ether (6 mmol) and di-isopropylcarbodiimole (6 mmol) were reacted with the leucine resin ester in $CH_2Cl_2$/DMF (35 ml) for 12 h then the Fmoc-Tyr(Bu$^t$)-Leu-resin ester was washed with $CH_2Cl_2$ (5×50 ml).

To remove the Fmoc protecting group, the peptide resin was washed with DMF (5×50 ml), reacted with 55% piperidine in DMF (50 ml) for 5 min then 20 min, then washed with DMF (5×50 ml).

Subsequent Fmoc amino acids were coupled using the procedure described above except for Fmoc-glutamine which was incorporated using the HOBT/DCC pre-activation procedure of König and Geiger (Chem. Ber., 103, 788–98, (1970)).

Couplings, in general, were carried out for 1–2 h and repeated if necessary. Completeness of acylation was verified by a qualitative ninhydrin test as described by E. Kaiser et al, in Anal. Biochem., (1970), p34.

Deprotection was carried out by reaction with 55% piperidine in DMF, as described above, followed by reaction with a mixture of TFA (45 ml), $CH_2Cl_2$ (45 ml), anisole (10 ml) and methionine (1 g) for 84 min. The peptide resin was then washed with $CH_2Cl_2$ (5×50 ml) and dried.

Peptide cleavage from the resin was accomplished via ammonolysis to provide the peptide amide. To this end, the peptide resin was stirred with ammonia-saturated methanol (120 ml) for 44 h, filtered and washed with methanol. Evaporation of the combined washings followed by lyophilisation from aqueous acetic acid gave the crude peptide amide. The ammonolysis was repeated if FAB mass spec showed the presence of peptide ester.

Purification was carried out via HPLC on a Lichoprep RP8 column (25×1.6 cm) with 0.1% aqueous TFA (A) and 90% acetonitrile/10% A (B) as a gradient from 0% B to 100% B over 60 min at 12 ml/min.

EXAMPLE 10

H-Lys-Gln-Met-Ala-Val-Lys-Lys-Tyr-Leu-NH$_2$.Acetate (XXXV)

[MH]$^+$ (FAB)=1007.

Amino acid analysis; Glu (0.92), Ala (0.92), Tyr (0.98), Val (0.99), Met (0.85), Leu (1.08), Lys (3.24).

EXAMPLE 11 AND 12

The following examples are prepared in accordance with the methods described for examples 3 to 9.

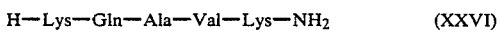  (XXVI)

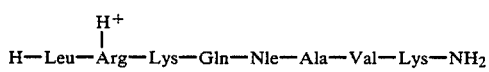  (XXVII)

PHARMACOLOGICAL DATA

I. Colonic Motility (a) In vivo

Male albino rats, Wistar strain (Charles River UK) 300–500 g were anaesthetised with urethane. A segment of proximal colon was prepared for intraluminal pressure recording after the method of Maggi and Meli (Maggi, C. A. and Meli, A. (1982), J. Pharmacol. Methods 8, 39–46). The activity of the compound (V) was assessed from its action on the spontaneous motility of the preparation after intravenous administration. The compound was found to be active at 3 μmol/kg.

(b) In vitro

Segments of circular muscle cut from the proximal colon of rats were mounted in Krebs solution in isolated tissue baths after the methods of Couture et al. (Couture R. et al. (1981), Can. J. Physiol. Pharmacol., 59, 957–964; and Couture R. et al., (1982), Pharmacol., 24, 230–242). The activity of the compound V was assessed from the effect on the spontaneous contractile responses generated by this tissue. The ED$_{50}$ was found to be 10$^{-5}$M.

II. Anti-ulcer Activity

Anti-ulcer activity may be related to the enhanced capacity to dispose of gastric acid. Acid disposal capacity may be enhanced by increased intestinal secretions and enhanced acid disposal capacity is believed to be useful in the treatment of peptic ulcer disease.

Method for estimating the acid disposal capacity of the rat proximal duodenum

Male Wistar rats, 180–250 g bodyweight, fasted overnight, are anaesthetized with urethane (150 mg/100 g bodyweight i.m.). The trachea is cannulated, and a gastric cannula, 0.5 cm i.d., 3 cm long, is inserted into the non-glandular forestomach via a mid-line abdominal incision. The intragastric cannula is exteriorized via a stab wound in the body wall. A triple lumen catheter, 0.3 cm o.d., is passed via the gastric cannula through the pylorus. The duodenum is ligated 1 cm below the pylorus, and the pylorus ligated around the cannula, thus creating a 1 cm proximal duodenal pouch excluding pancreatic and biliary secretions. The two ligatures enclosing the duodenal pouch are placed so as to avoid occluding the blood supply to the duodenal segment. Gastric secretions are allowed to drain freely from the gastric cannula. Compounds are administered dissolved in 0.9% sodium chloride (saline) as a 1.2 ml/h infusion via a catheter inserted in a jugular vein.

The triple lumen catheter is connected as follows. Lumen 1 delivers perfusing medium at 0.1 ml/min via a peristaltic pump.

Lumen 2 collects the perfusate and delivers it to a flow cell containing a pH microelectrode. Outflow pH is recorded throughout the experiment. Lumen 3 is connected to a pressure transducer to monitor intraluminal pouch pressure. Body temperature is maintained at 34° C. throughout the experiments.

After preparation, the duodenal segment is perfused with saline, adjusted to pH 6.5 with hydrochloric acid, for 30 minutes. The perfusing medium is then changed successively to saline adjusted with hydrochloric acid to pH 4, 3.5, 3 and 2.5 in increasing order of acidity. Each solution is perfused for 40 minutes. At the end of the pH 2.5 infusion period, saline pH 6.5 is perfused for 30 minutes, and the descending pH series repeated. This procedure produces two series of input pH/output pH values, designated 1st and 2nd passes.

A group size of 6 animals or larger is used and the effect of compounds on the output pH compared to control data determined. For comparisons between groups, Student's 't' test is used. Significance is taken at P<0.05.

The compound of example 4 caused a significant increase in acid disposal at input pH 3 and 2.5 on the first pass and input pH 2.5 on the second pass at a dose of 150 nmol/kg/h, and at input pH 2.5 on the first pass at a dose of 30 nmol/kg/h.

What is claimed is:

1. A polypeptide of the general formula $$X-(Y')_n-Y_{15}Y_{16}Y_{17}Y_{18}Y_{19}Y_{20}-(Y'')_m-Z$$

in which

X represents a hydrogen atom or an amine-protecting group, preferably a hydrogen atom;

(Y')$_n$ represents a direct bond or

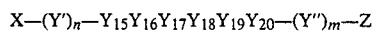

in which

Y$_{11}$ represents Thr, Ser or the residue of another naturally occurring hydroxy amino acid, $Y_{12}$ represents Arg or the residue of another naturally occurring basic amino acid, $Y_{13}$ represents Leu, Phe or the residue of another naturally occurring hydrophobic amino acid, $Y_{14}$ represents Arg or the residue of another naturally occurring basic amino acid;

$Y_{15}$ represents Lys or the residue of another naturally occurring basic amino acid, $Y_{16}$ represents Gln or the residue of another naturally occurring carboxamido amino acid, $Y_{17}$ represents Met or the residue of another naturally occurring neutral amino acid, $Y_{18}$ represents Ala or the residue of another naturally occurring hydrophobic amino acid, $Y_{19}$ represents Val or the residue of another naturally occurring hydrophobic amino acid, $Y_{20}$ represents Lys or the residue of another basic naturally occurring amino acid, $(Y'')_m$ represents a direct bond or $Y_{21}$, $Y_{21}Y_{22}$ or $Y_{21}Y_{22}Y_{23}$ in which $Y_{21}$ represents Lys or the residue of another basic naturally occurring amino acid, $Y_{22}$ represents Tyr or the residue of another naturally occurring hydrophobic amino acid, $Y_{23}$ represents Leu or the residue of another naturally occurring hydrophobic amino acid; and Z represents a hydroxyl group, or a group of the formula OR such COZ represents an ester, or a hydrazino group such that COZ represents a hydrazide, or $NH_2$ such that COZ represents an amide; and pharmaceutically acceptable salts thereof.

2. A peptide according to claim 1 wherein all the amino acid units are in the L-form.

3. A peptide or analogue according to claim 1 wherein the carboxy-terminus of the peptide or analogue is in the form of the unsubstituted amide.

4. A peptide or analogue according to claim 1 wherein the amino-terminus of the peptide is in the form of the unsubstituted amine.

5. The hexapeptide H-Lys-Gln-Y-Ala-Val-Lys-$NH_2$ or H-Lys-Gln-Y-Ala-Leu-Lys-$NH_2$, wherein Y represents Met or Nle.

6. H-Lys-Gln-Nle-Ala-Val-Lys-$NH_2$,
H-Arg-Lys-Gln-Nle-Ala-Val-Lys-Lys-$NH_2$,
H-Leu-Arg-Lys-Gln-Nle-Ala-Val-Lys-Lys-$NH_2$,
H-Lys-Gln-Nle-Ala-Leu-Lys-$NH_2$,
H-Lys-Gln-Nle-Ala-Val-Orn-$NH_2$,
H-Orn-Gln-Nle-Ala-Val-Orn-$NH_2$,
H-Lys-Gln-Leu-Ala-Val-Lys-$NH_2$,
H-Arg-Lys-Gln-Nle-Ala-Val-Lys-Lys-Tyr-Leu-$NH_2$,
H-Lys-Gln-Nle-Ala-Val-Lys-Lys-Tyr-Leu-$NH_2$,
H-Lys-Gln-Met-Ala-Val-Lys-Lys-Tyr-Leu-$NH_2$,
H-Lys-Gln-Nle-Ala-Val-Lys-Lys-$NH_2$ or $$H\text{—Leu—}\overset{\overset{H^+}{|}}{Arg}\text{—Lys—Gln—Nle—Ala—Val—Lys—}NH_2,$$

or a pharmaceutically acceptable salt of any of the foregoing.

7. A compound according to claim 1 in pharmaceutically acceptable form.

8. A pharmaceutical composition for treating peptic ulcer disease comprising an effective amount of a peptide or analogue according to claim 1 or a pharmaceutically acceptable salt thereof and a pharmaceutically acceptable carrier.

9. A method of treatment of peptic ulcer disease disorders in mammals, such as humans which comprises the administration of an effective amount of a peptide or analogue according to claim 1, or a pharmaceutically acceptable salt thereof.

* * * * *